United States Patent [19]

Metz, deceased et al.

[11] Patent Number: 4,892,531
[45] Date of Patent: Jan. 9, 1990

[54] ANTI-SEAL DEVICE FOR USE WITH OSTOMY APPLIANCES

[75] Inventors: Jack L. Metz, deceased, late of Des Plaines, Ill.; by Florence Metz, executrix, 469 Oak St., Des Plaines, Ill. 60016

[73] Assignee: Florence Metz, Des Plaines, Ill.

[21] Appl. No.: 95,212

[22] Filed: Sep. 11, 1987

[51] Int. Cl.⁴ .............................................. A61F 5/44
[52] U.S. Cl. .................................................... 604/340
[58] Field of Search ............. 604/277, 338, 339, 340, 604/341, 342, 343, 344, 345; 251/343–345

[56] References Cited

U.S. PATENT DOCUMENTS

| | | | |
|---|---|---|---|
| 2,563,597 | 8/1951 | Friedman | 604/339 |
| 2,656,838 | 10/1953 | McConnell | 604/340 |
| 2,874,697 | 2/1959 | Johnson | 604/340 |
| 3,561,487 | 2/1971 | Reed, Jr. | 251/345 |
| 4,636,206 | 1/1987 | Ederati | 604/340 |
| 4,721,508 | 1/1988 | Burton | 604/338 |

FOREIGN PATENT DOCUMENTS 732155 6/1955 United Kingdom .............. 604/338

*Primary Examiner*—Jerome L. Kruter
*Attorney, Agent, or Firm*—Welsh & Katz, Ltd.

[57] ABSTRACT

A sleeve-like element having at least one opening in a wall to permit the flow of body wastes from a stoma to a pouch while preventing a wall of the pouch from blocking the discharge end of said stoma. Said sleeve-like element protects the stoma from accidental external forces and allows a user to firm up the critical adhesive area surrounding the stoma following the attachment and assembly of the system. The sleeve-like element is readily cleanable for re-use.

3 Claims, 2 Drawing Sheets

ANTI-SEAL DEVICE FOR USE WITH OSTOMY APPLIANCES

1. Field of Invention

This invention relates to medical ostomy devices wherein a storage pouch is attached to the body of an individual to collect excreted waste product in lieu of normal body facilities.

2. Background Art

A typical commercially available ostomy system includes a diaphragm which is placed against the body of the user and held by an adhesive. The diaphragm has a centrally located aperture, which surrounds the stoma through which body waste materials exit, and a molded plastic ring concentric with the aperture.

A pouch, having a plastic molded ring attached to an opening in one side wall, is placed over the diaphragm ring and pressed so that the two rings (one being male, the other-female) form a water tight connection, or passageway, from the stoma to the pouch.

The assembly procedure, for the described system, involves preparing the person's skin in the attachment area with an adhesive enhancement agent, allowing it to dry and then pressing the diaphragm into place against the person's body. The condition of the adhesive area inside the molded diaphragm ring and immediately surrounding the stoma, is critical in that it must be firmly pressed against the body to achieve an optimum seal and best diaphragm adherence. This area is difficult to adequately cover with the user's fingers and so during the diaphragm attachment time interval the stoma, over which the user has no control, may discharge the body wastes. For this reason one usually learns to sacrifice a better body to diaphragm attachment condition in favor of closing the system by attaching the pouch as rapidly as possible. Since the outer wall of the pouch now covers the passageway, this further complicates the pressing of the adhesive in the aforementioned critical area.

In addition to the described adhesive problem, the outer wall of the pouch can seal the passageway if the waste material has any sticky constituents, or if clothing, seat belts, and/or other external forces and hold the outer wall of the pouch against the attachment ring so as to block the flow of material. When the system is so blocked, the pressure in the expelled material can build up and cause an opening in the attachment ring connection. Such condition usually results in soiling the user's body, the outer garments and/or the bedding. The latter being of a special concern for those who sleep or lie on their stomachs.

Additionally, such diaphragm and pouch systems, as previously described, offer little or no effective protection to the stoma from accidental external forces such as collisions with protrusions of furniture, factory machinery, kitchen appliances, articles of clothing, and/or flying objects, all of which can be potentially injurious to the stoma.

DISCLOSURE OF THE INVENTION

In accordance with the present invention, I provide means for preventing the ostomy from sealing its own opening and causing internal blockage in the system, protecting the stoma from external potentially injurious forces, and enabling an individual to apply pressure to the critical adhesive area following assembly and attachment of the system to the body.

The present invention relates to a sleeve-like element being larger in internal size than the stoma, and smaller in overall size than the diaphragm, or wafer, and pouch coupling rings, and having at least one opening in its wall to permit the flow of body waste products. In the preferred embodiment of the invention the device comprises a separate cup-like element having one fully or partially closed end which is placed in facing relationship with the outer wall of the pouch thus forming a protective cover for the stoma.

THE DRAWINGS

FIG. 1 is an expanded view of the ostomy system showing the relative positions of the diaphragm 10, the anti-seal device 20, and the pouch 30.

DETAILED DESCRIPTION

Figure 1:
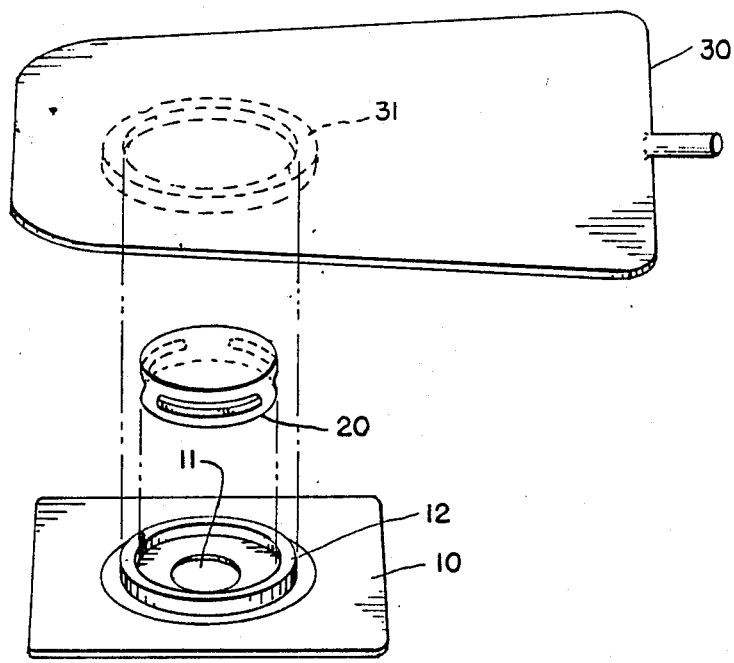

Referring now to the drawing for better undrstanding of the present invention, more specifically to FIG. 1 which shows an expanded view of the system comprising an adhesive backed diaphragm 10, an anti-seal sleeve-like element 20, and a body waste storage pouch 30.

Figure 2:
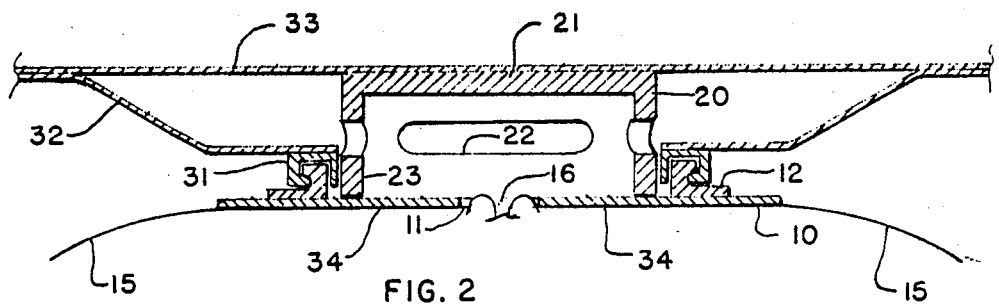
FIG. 2 is a cross-sectional view of the assembly of the system with the anti-seal device of the present invention.

FIG. 2 presents a cross-sectional view of the assembled ostomy system for greater clarity, and attached to the body 15 and centrally located over the body stoma 16. The diaphragm 10 has an aperture 11 through which the body stoma 16 protrudes. The aperture 11 is surrounded by a ring 12 which is coupled to a pouch ring 31. The pouch ring 31 is located in the inner most pouch wall 32. The anti-seal sleeve-like element 20, shown in the preferred form as having a closed end 21, has openings 22 in the side wall 23 through which body waste materials pass on the way from the stoma 16 to the storage pouch 31. The anti-seal sleeve-like element 20 is of sufficient material thickness so as to be self supporting and of sufficient overall thickness so as to hold the outer wall 33 of the pouch 30 away from the opening of the coupling ring 31, thus preventing a blockage which would prevent proper flow of body waste products into the pouch 30. As best seen in FIG. 2, the closed end 21 of the anti-seal sleeve-like element 20 provides a solid protective cover for the sensitive and vulnerable stoma 16. FIG. 2 also shows how externally applied finger pressure can be conveyed to the critical adhesive area 34, described on page 1, lines 23 and 24, by the anti-seal sleeve-like element 20.

Figure 3:
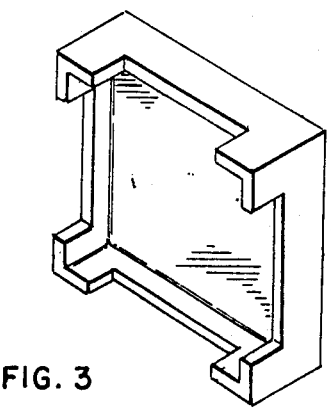
FIG. 3 is a perspective view of another embodiment of the anti-seal device.

FIG. 3 shows another embodiment of the anti-seal sleeve-like element of the present invention.

Figure 4A:
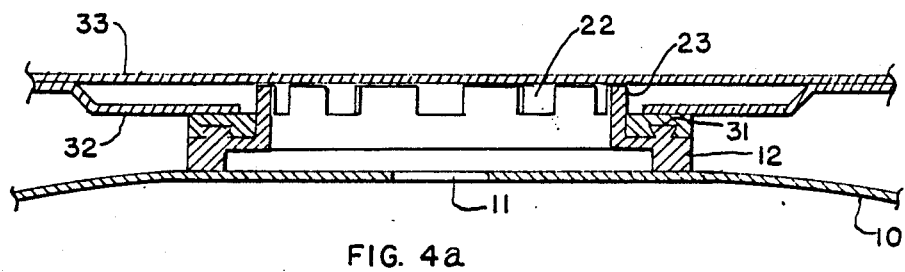
FIGS. 4a and 4b are cross-sectional views of the anti-seal device formed as an integral part of either the diaphragm coupling ring or of the pouch coupling ring.
Figure 4B:
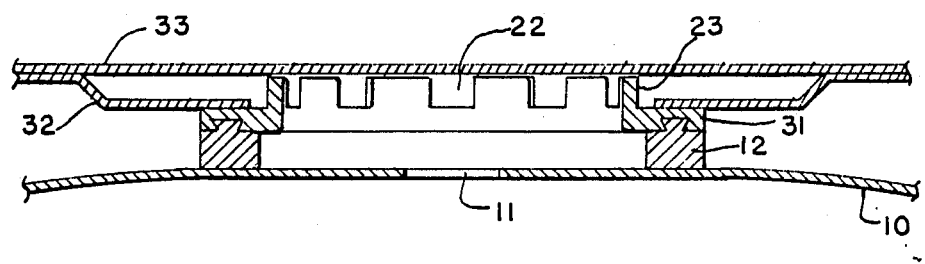

FIGS. 4a and 4b represent still other embodiments and show how the sleeve-like element might be incorporated into the diaphragm or pouch rings as an integral part of either.

What is claimed is:

1. An improved ostomy appliance for collecting waste material emitted from a human body through a stoma, said appliance comprising:
   a diaphragm having an aperture adapted to permit the stoma to enter and project slightly therethrough;
   first means for attaching said diaphragm to the body;

a pouch having an inner wall and an outer wall, said walls being joined along peripheral edge margins thereof for storing body waste materials emitted from the stoma, said inner wall having an opening to allow the entrance of the waste material into said pouch, said pouch opening being in register with said diaphragm aperture;

second means for attaching said pouch to said diaphragm so as to define a passageway adapted to allow the passage of the waste material from the stoma into said pouch;

a cup-like anti-seal device located within said pouch between said outer wall and said diaphragm and having a completely closed end which faces said pouch outer wall, a cylindrical side wall peripherally secured at one end thereof to said closed end, said side wall having at least one opening therein and a thickness sufficient to maintain said outer pouch wall away from the stoma, said side wall defining an open end of said device opposite said closed end, said open end positioned within said pouch to contact said diaphragm, to be inserted into said opening and to circumscribe the stoma so as to maintain said outer wall away from the stoma, such that externally applied pressure to said closed end is conveyed around the entire periphery of the stoma and the stoma is protected from direct impact.

2. The appliance defined in claim 1 wherein said sidewall is provided with three elongate openings therein.

3. The appliance defined in claim 1, wherein said closed end of said side wall is coaxial with said aperture of said diaphragm.

* * * * *